(12) United States Patent
Mooney et al.

(10) Patent No.: US 11,887,716 B2
(45) Date of Patent: Jan. 30, 2024

(54) INFUSION MANAGEMENT SYSTEM

(71) Applicant: CareFusion 303, Inc., San Diego, CA (US)

(72) Inventors: Keith Mooney, Limerick (IE); Kevin O'Brien, Thurles (IE); Christopher Coleman, Limerick (IE); Dara George, Shannon (IE); Ehab Azab, Limerick (IE)

(73) Assignee: CareFusion 303, Inc., San Diego, CA (US)

( * ) Notice: Subject to any disclaimer, the term of this patent is extended or adjusted under 35 U.S.C. 154(b) by 349 days.

(21) Appl. No.: 17/227,128

(22) Filed: Apr. 9, 2021

(65) Prior Publication Data

US 2021/0358589 A1 Nov. 18, 2021

Related U.S. Application Data

(60) Provisional application No. 63/039,386, filed on Jun. 15, 2020, provisional application No. 63/008,149, filed on Apr. 10, 2020.

(51) Int. Cl.
*G16H 20/17* (2018.01)
*A61M 5/142* (2006.01)
*G06F 21/62* (2013.01)
*G06F 21/31* (2013.01)

(52) U.S. Cl.
CPC ............ *G16H 20/17* (2018.01); *A61M 5/142* (2013.01); *G06F 21/31* (2013.01); *G06F 21/6245* (2013.01); *A61M 2005/14208* (2013.01); *A61M 2205/3553* (2013.01); *A61M 2205/52* (2013.01);

(Continued)

(58) Field of Classification Search
CPC ....... G16H 20/17; G16H 40/67; A61M 5/142; A61M 2005/14208; A61M 2205/3553; A61M 2205/52; A61M 2205/583; A61M 2205/60; A61M 5/172; A61M 2205/3592; A61M 2205/50; A61M 5/14; G06F 21/31; G06F 21/6245
See application file for complete search history.

(56) References Cited

U.S. PATENT DOCUMENTS

| 10,226,571 B2 | 3/2019 | Davis et al. |
| 2009/0099867 A1* | 4/2009 | Newman ................ G16H 40/20 705/2 |

(Continued)

*Primary Examiner* — Amber R Stiles
*Assistant Examiner* — Nelson Louis Alvarado, Jr.
(74) *Attorney, Agent, or Firm* — Mintz Levin Cohn Ferris Glovsky and Popeo, P.C.

(57) ABSTRACT

A method includes receiving, by a master infusion device from a server, at least one fluid delivery protocol. The fluid delivery protocol includes one or more parameters for delivering a fluid to a user. The method also includes configuring, by the master infusion device, a first slave infusion pump with a first fluid delivery protocol of the at least one fluid delivery protocol. The method further includes configuring, by the master infusion device, a second slave infusion pump with a second fluid delivery protocol of the at least one fluid delivery protocol. The method also includes delivering, by the first slave infusion pump and based on the first fluid delivery protocol, the fluid to the user. Related methods and articles of manufacture, including apparatuses and computer program products, are also disclosed.

20 Claims, 12 Drawing Sheets

(52) U.S. Cl.
CPC ... *A61M 2205/583* (2013.01); *A61M 2205/60* (2013.01)

(56) References Cited

U.S. PATENT DOCUMENTS

| | | | |
|---|---|---|---|
| 2016/0074573 A1* | 3/2016 | Kohlbrecher | A61M 5/172 604/151 |
| 2016/0256622 A1* | 9/2016 | Day | A61M 5/172 |
| 2019/0111209 A1 | 4/2019 | Murphy, Jr. et al. | |

* cited by examiner

INFUSION MANAGEMENT SYSTEM

CROSS-REFERENCE TO RELATED APPLICATIONS

The present application claims priority to U.S. Provisional Application No. 63/039,386, filed on Jun. 15, 2020, and entitled "INFUSION MANAGEMENT SYSTEM," and U.S. Provisional Application No. 63/008,149, filed on Apr. 10, 2020, and entitled "INFUSION MANAGEMENT SYSTEM," the entirety of each of which is incorporated by reference herein.

TECHNICAL FIELD

The subject matter described herein relates generally to the dispensation of medications and more specifically to an infusion management system for the delivery of medication to a patient.

BACKGROUND

Fluid pumps, such as infusion pumps, administer therapy to patients by delivering a medication or other fluid to the patient. In some instances, a particular type of therapy, such as chemotherapy, may require multiple fluid pumps. The fluid pumps may be large, making it difficult to store and/or use the pumps, as the available space in a medical facility or patient care room may be limited. Additionally and/or alternatively, certain types of therapy, such as the delivery of insulin, may be delivered to the patient at a location other than the medical facility, such as at the patient's home, or while the patient is traveling. As a result, administering therapy to patients at locations other than at the medical facility may be difficult due to the poor portability of the pumps and the inability for the pumps to be remotely controlled. Even in circumstances in which pumps may be remotely controlled, providing relevant information to the patient about the pump or the administered therapy may be difficult.

SUMMARY

Systems, methods, and articles of manufacture, including computer program products, are provided for an infusion management system for dispensing a medication to a patient. For example, the system may provide a portable slave infusion pump that may be easily carried and/or worn by the user. The slave infusion pump may receive a fluid delivery protocol from a master infusion pump, which may also be used to transmit particular fluid delivery protocols to one or more other slave infusion pumps.

According to some aspects, a method may include receiving, by a master infusion device from a server, at least one fluid delivery protocol. The fluid delivery protocol may include one or more parameters for delivering a fluid to a user. The method may also include configuring, by the master infusion device, a first slave infusion pump with a first fluid delivery protocol of the at least one fluid delivery protocol. The method may also include configuring, by the master infusion device, a second slave infusion pump with a second fluid delivery protocol of the at least one fluid delivery protocol. The method may also include delivering, by the first slave infusion pump and based on the first fluid delivery protocol, the fluid to the user.

In some aspects, the first slave infusion pump is communicatively coupled with a user device. The user device may display at least one of the one or more parameters for delivering the fluid to the user.

In some aspects, the first slave infusion pump does not comprise a display.

In some aspects, the method also includes measuring, by the first slave infusion pump, one or more fluid delivery parameters associated with the delivery of the fluid. The method may also include transmitting, by the first slave infusion pump to a user device in wireless communication with the first slave infusion pump, the one or more fluid delivery parameters. The method may further include transmitting, by the user device to the server, the one or more fluid delivery parameters.

In some aspects, the receiving further includes authenticating a clinician to provide access to the fluid delivery protocol on the server.

In some aspects, the configuring the first slave infusion pump includes establishing a secure connection between the first slave infusion pump and the master infusion device. The establishing may include encrypting transmissions between the first slave infusion pump and the master infusion device.

In some aspects, the first fluid delivery protocol is different from the second fluid delivery protocol. The first slave infusion pump may be configured to deliver the fluid to a first user based on the first fluid delivery protocol. The second slave infusion pump may be configured to deliver the fluid to a second user based on the second fluid delivery protocol.

In some aspects, the method also includes detecting an error in the delivery of the fluid to the user. The method may also include stopping the delivery of the fluid to the user.

In some aspects, the method also includes transmitting the error to a user device in wireless communication with the first slave infusion pump. The method may also include displaying information associated with the error via the user device.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a slave pump system, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
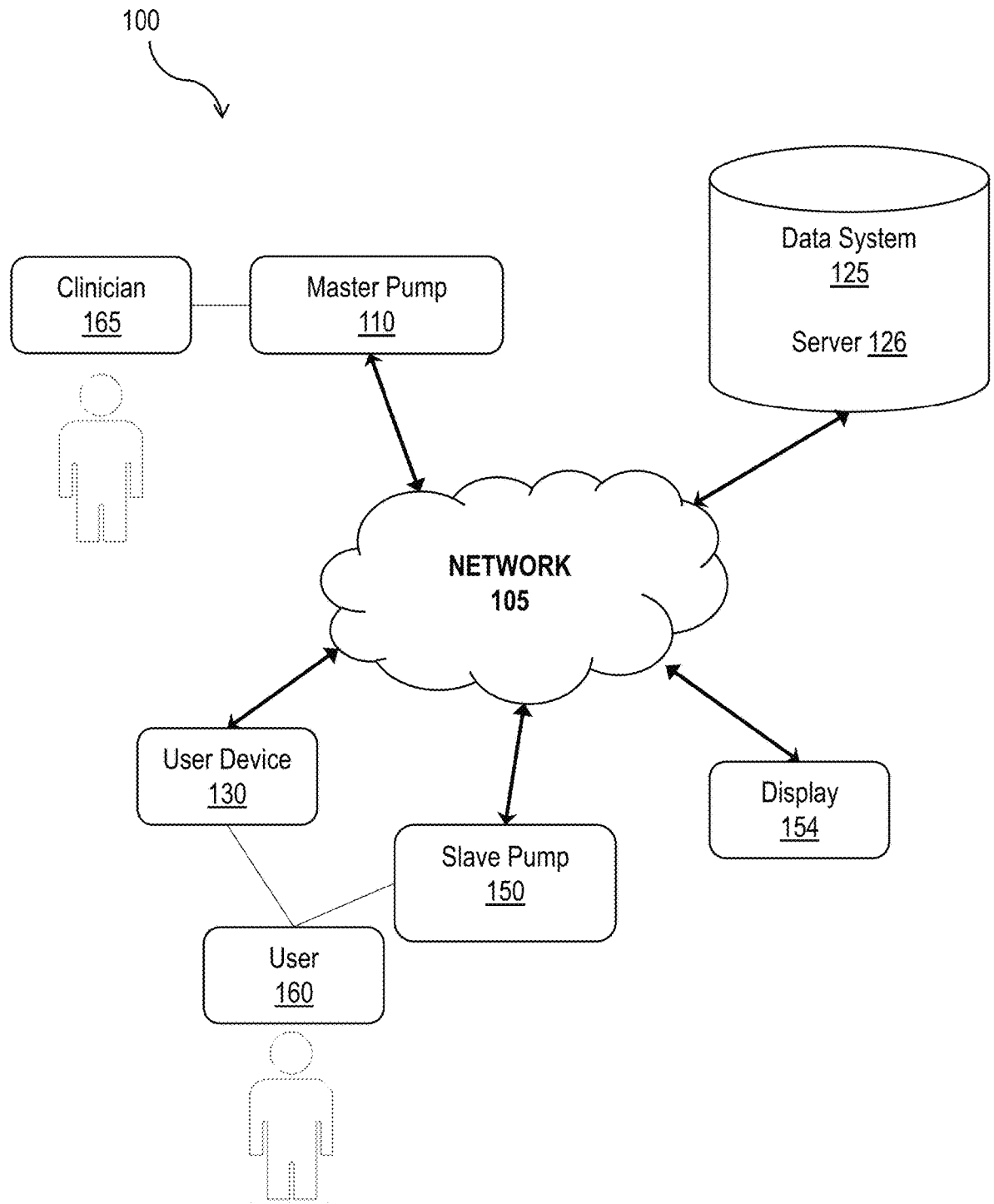
FIG. 1 depicts a system diagram illustrating an infusion management system, in accordance with some example embodiments.

Fluid pumps, such as infusion pumps, administer therapy to patients by delivering a medication or other fluid to the patient. The delivery of certain therapies may require multiple pumps and/or multiple-channel pumps, such as during the delivery of chemotherapy. These pumps may be very large, occupy a large amount of space within a hospital and/or patient care room, and may be very cumbersome to use. For example, during cancer treatments, the administration of chemotherapy may be combined with one or more other treatments, such as hydration treatments. The infusion management system described herein includes one or more wireless slave infusion devices, such as slave infusion pumps, which may be smaller than the pumps (e.g., multi-channel pumps) generally used for delivering certain therapies, such as chemotherapy or other therapies during which multiple types of fluid therapies may be combined. For example, the slave infusion pumps may include a user interface having an indicator and power button, without a display. By reducing the size of the slave infusion pumps, a greater number of pumps may be stored within a medical facility and/or patient care room, making it easier to deliver therapies that include the delivery of multiple types of fluid, and improving the flexibility in these types of treatments.

Reducing the size of the pumps, such as by providing the slave infusion pump described herein, may allow the pumps to be located adjacent to and/or closer to the infusion site on the patient's body. This reduces the risk of incorrect and/or displaced connection in the fluid delivery lines connecting the slave infusion pump to the patient's body, as the pump is located closer to the infusion site. This may also reduce influence of the fluid delivery line on the administration of the fluid therapy to the patient. As a result, the slave infusion pumps described herein may improve the accuracy of measurements made based on the delivered therapy.

Additionally and/or alternatively, certain types of therapy, such as the delivery of insulin, may be delivered to the patient at a location other than at the medical facility, such as at the patient's home, or while the patient is traveling. As noted above, fluid pumps may generally be very large, making it difficult to store and/or use the pumps. Thus, administering therapy to patients at locations other than at the medical facility may be difficult due to the poor portability of the pumps and the inability for the pumps to be remotely controlled. Even in circumstances in which pumps may be remotely controlled, providing relevant information to the patient about the pump or the administered therapy may be difficult. The infusion management system including the slave infusion pumps described herein may allow patients to receive fluid therapy in their homes, rather than at a medical facility, leading to a more comfortable life, and improved experience receiving the fluid therapy. The slave infusion pumps described herein may also be worn on a patient's body and/or easily carried by the patient, allowing the patient to receive the administered therapy at various locations. In some implementations, the slave infusion pumps described herein may also be remotely controlled by an application on a mobile device or standalone display and/or transmit useful data about the administered therapy to the mobile device to be displayed to the patient and/or be transmitted to the medical facility. Such configurations may make it easier for the patients (or caregivers thereof) to use the slave infusion pumps to administer the fluid therapy, may help to reduce the size of the slave infusion pumps by eliminating the need for a display on the pumps, and may help to improve the portability of the slave infusion pumps. Such configurations may additionally and/or alternatively reduce the cost of the slave infusion pumps, as the pumps may include a reduced set of components. Such configurations may provide a consolidated interface that is easier to use for the patient. The consolidated interface (e.g., via the separate display) may be easier to use and/or read by the patient. Using the consolidated interface, rules may be implemented by the medical care provider to prevent the administration of incompatible fluids to the patient.

The infusion management system described herein may control communication between one or more large volume infusion devices (e.g., pumps) to enable a master-slave protocol, in which the master infusion device, such as the one or more large volume infusion devices, may control multiple slave infusion devices (e.g., pumps). In other words, a single interface (e.g., the large volume infusion device) may be used to control operation of one or more slave infusion devices to be used by a patient or user.

FIG. 1 depicts a system diagram illustrating an infusion management system 100, in accordance with some example implementations. Referring to FIG. 1, the infusion management system 100 may include a master infusion pump 110

(also referred to herein as a "master infusion device"), a slave infusion pump 150 (also referred to herein as a "slave infusion device"), a user device 130, a display 154, and a data system 125.

The display 154 may form a part of the user device 130 or may be separately coupled to the slave infusion pump 150. The display 154 may also include a user interface. The user interface may form a part of a display screen of the display 154 that presents information to a user 160 (e.g., a patient or caregiver thereof such as a family member or home healthcare assistant) and/or the user interface may be separate from the display screen. For example, the user interface may be one or more buttons, or portions of the display screen that is configured to receive an entry from the user 160.

The user device 130 may be a mobile device such as, for example, a smartphone, a tablet computer, a wearable apparatus, and/or the like. However, it should be appreciated that the user device 130 may be any processor-based device including, for example, a desktop computer, a laptop computer, a workstation, a network-connected television, and/or the like. For example, via the user device 130, the user 160 may be able to view certain parameters of the slave infusion pump 150, such as information relating to the user, the fluid therapy being delivered (e.g., a time or time interval of the fluid therapy delivery, an amount of fluid being delivered, a type of fluid being delivered, and/or the like), and/or an alert generated based on the slave infusion pump 150. The user device 130 may additionally and/or alternatively be used by a clinician 165 to configure certain parameters of the slave infusion pump 150, such as a time or time interval of the fluid therapy delivery, an amount of fluid being delivered, a type of fluid being delivered, and/or the like. Additionally, in some examples, via the user device 130, the clinician 165 may configure various fluid delivery protocols with default settings and safety parameters (e.g., setting a limit to a dose of a delivered fluid).

The data system 125 may include one or more databases, providing physical data storage within a dedicated facility and/or being locally stored on the master infusion pump 110. The data system 125 may include an inventory system, a patient care system, an administrative system, an electronic medical record system, and/or the like, which store a plurality of electronic medical records, each of which include the patient's medical history, one or more fluid delivery protocols, and/or the like. Additionally and/or alternatively, the data system 125 may include cloud-based systems providing remote storage of data in, for example, a multi-tenant computing environment and/or the like. The data system 125 may also include non-transitory computer readable media.

In some implementations, the data system 125 may include and/or be coupled to a server 126, which may be a server coupled to a network, a cloud server, and/or the like. The user device 130 may wirelessly communicate with the server 126. The server 126 may communicate directly with the master infusion pump 110 or through the user device 130. The server 126, which may include a cloud-based server, may provide data and/or instructions from the data system 125 to the master infusion pump 110 and/or the user device 130 to be transmitted to the slave infusion pump 150, to implement one or more features of the fluid therapy protocols consistent with implementations of the current subject matter. Additionally and/or alternatively, the server 126 may receive data (e.g., one or more parameters of the fluid therapy) from the user device 130 and/or the master infusion pump 110 that has been transmitted from the slave infusion pump 150.

Figure 4:
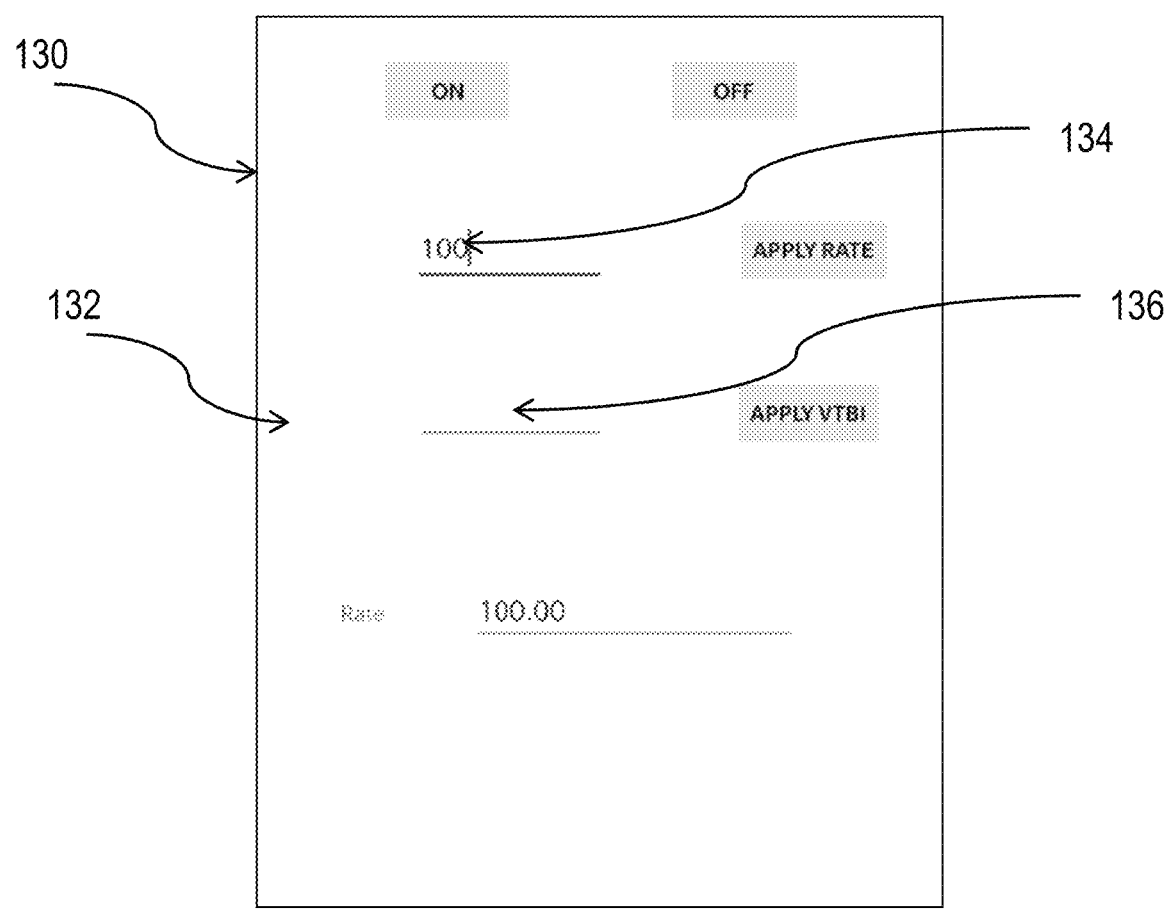
FIG. 4 depicts an example display of a user device, in accordance with some example embodiments.

An application software ("app") running on at least one of the user device 130 and/or the master infusion pump 110 may be configured to control operational aspects of the slave infusion pump 150, and receive information relating to operation of the slave infusion pump 150. For example, the app may provide the user 160 with a limited set of functionalities, such as viewing a status of the slave infusion pump 150, one or more parameters of the fluid therapy being delivered by the slave infusion pump 150, an error in the administration of the fluid therapy, and/or the like. FIG. 4 depicts an example of a user interface 132 of the app of the user device 130. The app may display, via the user interface 132, one or more parameters of the fluid therapy, such as a fluid delivery rate 134, a Volume to Be Infused (VTBI) 136, and/or the like. In some implementations, the app may additionally and/or alternatively provide the clinician 165 with capabilities to, via the app, retrieve one or more fluid delivery protocols from the server 126, establish a secure connection between the app, the master infusion pump 110, and/or the slave infusion pump 150, and transmit the fluid delivery protocols to the slave infusion pump 150. The app may also provide the clinician 165 with functionality to select one or more sets of properties or parameters of the fluid delivery protocols transmitted to the slave infusion pump 150. In some implementations, as described in more detail below, the app may log various parameters of the fluid therapy delivery by the slave infusion pump 150, and transmit the logged parameters to the master infusion pump 110 and/or the server 126.

The master infusion pump 110, the slave infusion pump 150, the user device 130, the display 154, and/or the data system 125 may be communicatively coupled to one another via a network 105. The network 105 may be a wired and/or wireless network including, for example, a public land mobile network (PLMN), a local area network (LAN), a virtual local area network (VLAN), a wide area network (WAN), the Internet, a short range radio connection, for example Bluetooth, a peer-to-peer mesh network, and/or the like.

The master infusion pump 110 may be a target controlled infusion (TCI) pump, a syringe pump, an anesthesia delivery pump, a patient-controlled analgesic (PCA) pump, a large volume pump (LVP), a small volume pump (SVP), and/or the like, configured to deliver a fluid (e.g., a medication) to a patient. However, it should be appreciated that the master infusion pump 110 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the master infusion pump 110 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Moreover, the master infusion pump 110 may be part of a patient care system that includes one or more additional pumps.

Likewise, the slave infusion pump 150 may be a TCI pump, a syringe pump, an anesthesia delivery pump, a patient-controlled analgesic (PCA) pump, a large volume pump (LVP), a small volume pump (SVP), and/or the like, configured to deliver a medication to a patient. However, it should be appreciated that the slave infusion pump 150 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the slave infusion pump 150 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Moreover, the slave infusion pump 150 may be part of a patient care system that includes one or more additional pumps.

Figure 3A:
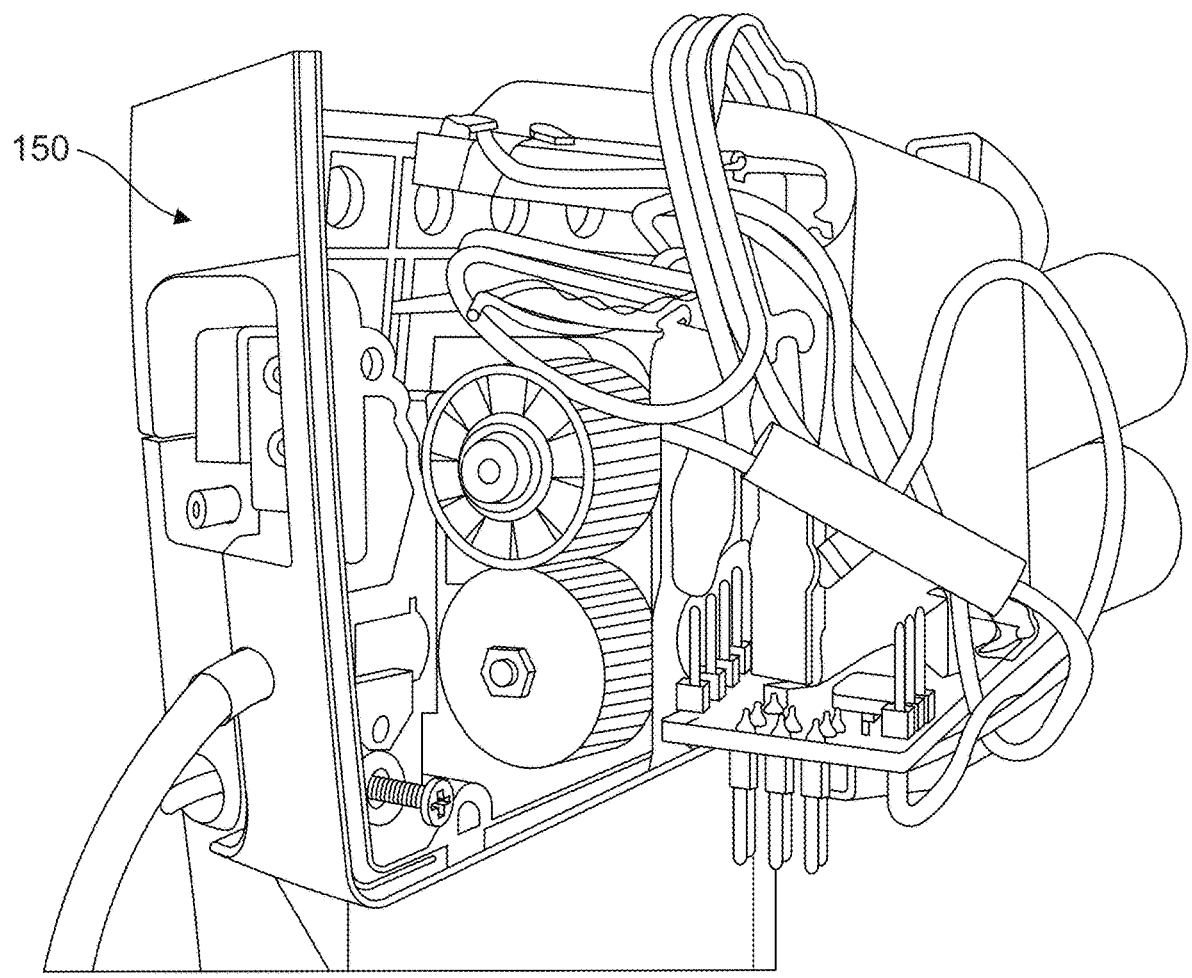
FIG. 3A depicts an example slave pump, in accordance with some example embodiments.
Figure 3B:
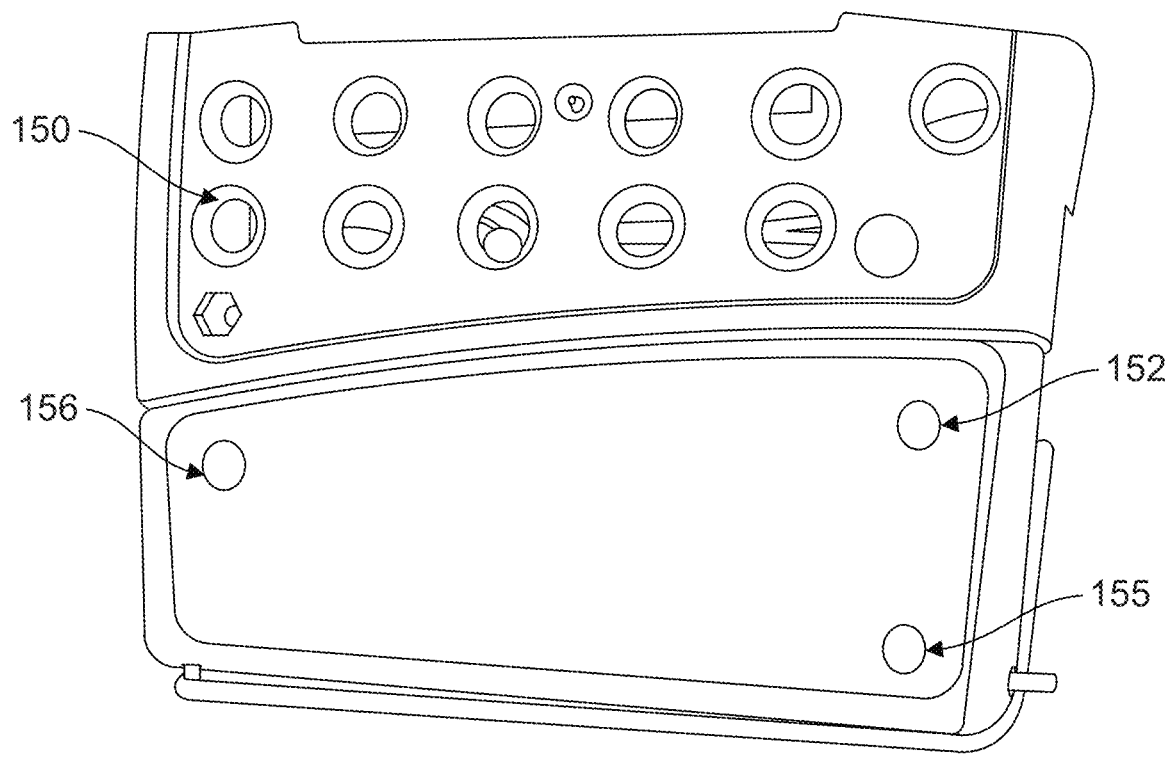
FIG. 3B depicts an example slave pump, in accordance with some example embodiments.

Unlike the master infusion pump 110, the slave infusion pump 150 may have limited functionality and/or features usable by the user 160. For example, FIGS. 3A and 3B illustrate an example of the slave infusion pump 150, consistent with implementations of the current subject matter. In some implementations, the slave infusion pump 150 does not have a display. Rather, the slave infusion pump 150 includes a limited user interface. The limited user interface of the slave infusion pump 150 may include one or more power buttons 152, a visual indicator 155 for providing visual feedback to the user (e.g., a light, etc.), and/or a pairing button 156 for pairing the slave infusion pump 150 to the user device 130 and/or the master infusion pump 110. The slave infusion pump 150 may additionally and/or alternatively include an audio indicator for providing an alert and/or an alarm, a wireless system on chip (SOC) for motor and/or feedback control within the body of the slave infusion pump 150, and a storage, which stores the fluid delivery protocols. Accordingly, as shown in FIGS. 3A and 3B, the slave infusion pump 150 may have a reduced profile, allowing the slave infusion pump 150 to be carried and/or worn by the user, and limiting the amount of space occupied by the slave infusion pump 150.

Figure 2:
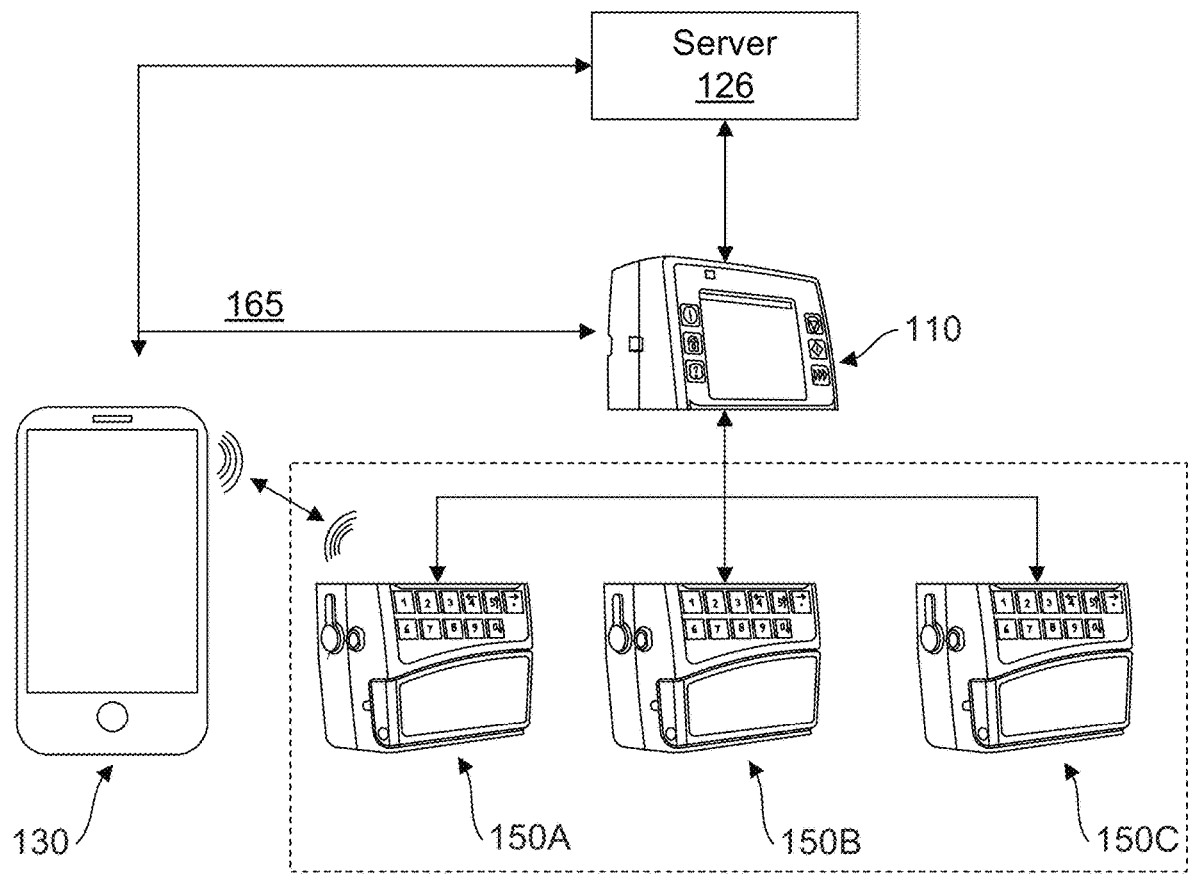
FIG. 2 schematically depicts a slave pump system, in accordance with some example embodiments.

FIG. 2 schematically illustrates an example of the infusion management system 100. The infusion management system 100 includes the server 126, the master infusion pump 110, the user device 130 including the app, and one or more slave infusion pumps 150. The one or more slave infusion pumps 150 may include one, two, three, four, five, six, or more slave infusion pumps 150. For example, the one or more slave infusion pumps 150 may include a first slave infusion pump 150A, a second slave infusion pump 150B, and a third slave infusion pump 150C. The first, second, and third slave infusion pumps 150A, 150B, 150C may have a reduced profile and may be easily carried and/or worn by the user, reducing the amount of space the pumps occupy in a medical facility, allowing the pumps to be located closer to the infusion site on the patient's body to provide more accurate measurements and reduce the likelihood that the pumps will be disconnected from the patient, improving the portability of the pumps to allow patients to more comfortably use the pumps away from the medical facility, and decreasing the cost of manufacturing the pumps.

Consistent with implementations of the current subject matter, the first, second, and third slave infusion pumps 150A, 150B, 150C may each receive a separate fluid delivery protocol from the master infusion pump 110 and/or the app on the user device 130. For example, the master infusion pump 110 and/or the app on the user device 130 may communicate with the server 126 to retrieve at least one fluid delivery protocol (e.g., one, two, three, four, five or more fluid delivery protocols). For example, the master infusion pump 110 and/or the app on the user device 130 may retrieve a first fluid delivery protocol, a second fluid delivery protocol, and/or a third fluid delivery protocol from the server 126. The at least one fluid delivery protocol may include one or more parameters for delivering a fluid to the user. The one or more parameters may include a volume of fluid to be delivered to the user, a type of fluid to be delivered to the user, a time interval of fluid delivery, a delivery rate of the fluid to be delivered to the user, a target concentration of the fluid to be delivered to the user, and/or the like.

Figure 6:
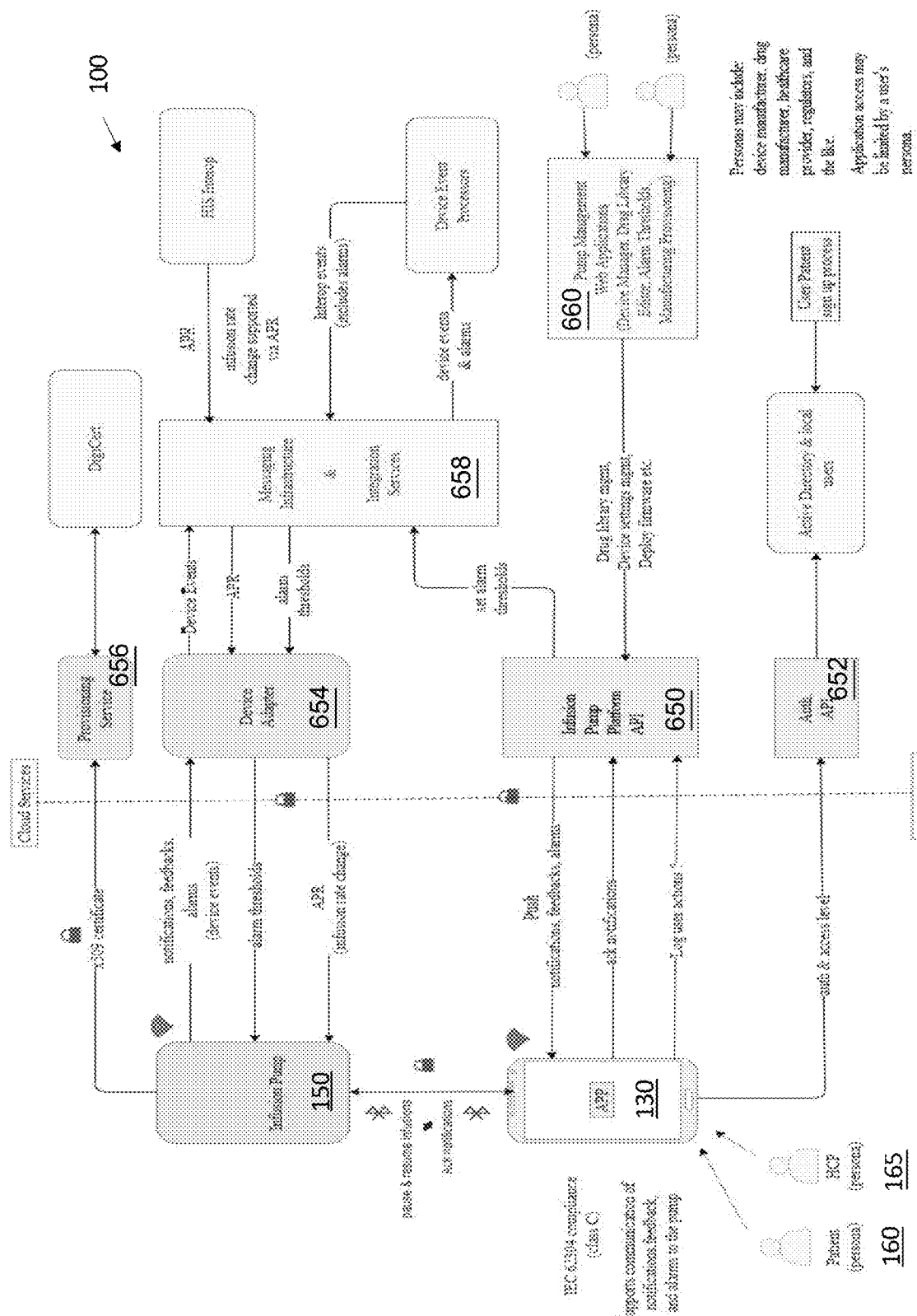
FIG. 6 schematically depicts an infusion management system, in accordance with some example embodiments.

The server 126 may include or be coupled to one or more data systems, including an inventory system, a patient care system, an administrative system, an electronic medical record system, and/or the like, which store a plurality of electronic medical records. Thus, the master infusion pump 110 and/or the app on the user device 130 may retrieve the one or more fluid delivery protocols from the inventory system, the patient care system, the administrative system, and/or the electronic medical record system. In some implementations, the master infusion pump 110 may be operated by the clinician 165 to retrieve the one or more fluid delivery protocols from the server 126. Additionally and/or alternatively, the app of the user device 130 may be operated by the clinician 165 to retrieve the one or more fluid delivery protocols from the server 126. To ensure that the user 160 is unable to retrieve and/or alter the one or more fluid delivery protocols via the app, the app may include one or more authentication features (such as via communication with an authorization API 652 as shown in FIG. 6) to allow the clinician 165 access to the server 126, and to prevent the user 160 from accessing certain features (e.g., the retrieval and/or altering of a fluid delivery protocol) of the app. For example, the app may prompt, via the user interface 132 of the user device 130, the clinician 165 enter a user name and password, scan a badge, perform a fingerprint scan or a retina scan, and/or use facial recognition to identify the clinician 165, to provide access, via the app, to retrieve and/or alter one or more aspects of the fluid delivery protocols.

The master pump 110 and/or the app may establish a secure communication channel with the first, second, and third slave infusion pumps 150A, 150B, 150C. In some implementations, the master pump 110 may establish a secure communication channel with the first, second, and third slave infusion pumps 150A, 150B, 150C sequentially and/or at the same time. For example, the master pump 110 may first establish a secure communication channel with the first slave infusion pump 150A and configure the first slave infusion pump 150A, then establish a secure communication channel with the second slave infusion pump 150B and configure the second slave infusion pump 150B, then establish a secure communication channel with the third slave infusion pump 150C and configure the third slave infusion pump 150B, and so on. The secure communication channel may include applying a digital signature or other authentication key that verifies the integrity of the information exchanged via the session. The first, second, and third slave infusion pumps 150A, 150B, 150C may detect that the secure channel is established with the master pump 110 and/or the app and provide a perceivable indication of the secure session on the first, second, and third slave infusion pumps 150A, 150B, 150C, such as via the visual indicator 155 (e.g., a change in color of the visual indicator, a blinking light of the visual indicator, a pattern displayed by the visual indicator, and/or the like). Similarly, the master infusion pump 110 and/or the app may determine that a secure channel is established with the first, second, and third slave infusion pumps 150A, 150B, 150C and provide a perceivable indication of the secure session on a display of the master infusion pump 110 and/or the app. The perceivable indication on the master infusion pump 110 and/or the app may include displaying an icon, changing a color on the user interface of the master infusion pump 110 and/or the app (e.g., the frame), activating a light on the master infusion pump 110 and/or the app, emitting an audible tone, or some combination of these or similar indicators. The detection of a secure session may be based on protocol messaging or information included in a message received from another device participating in the session.

Figure 5:
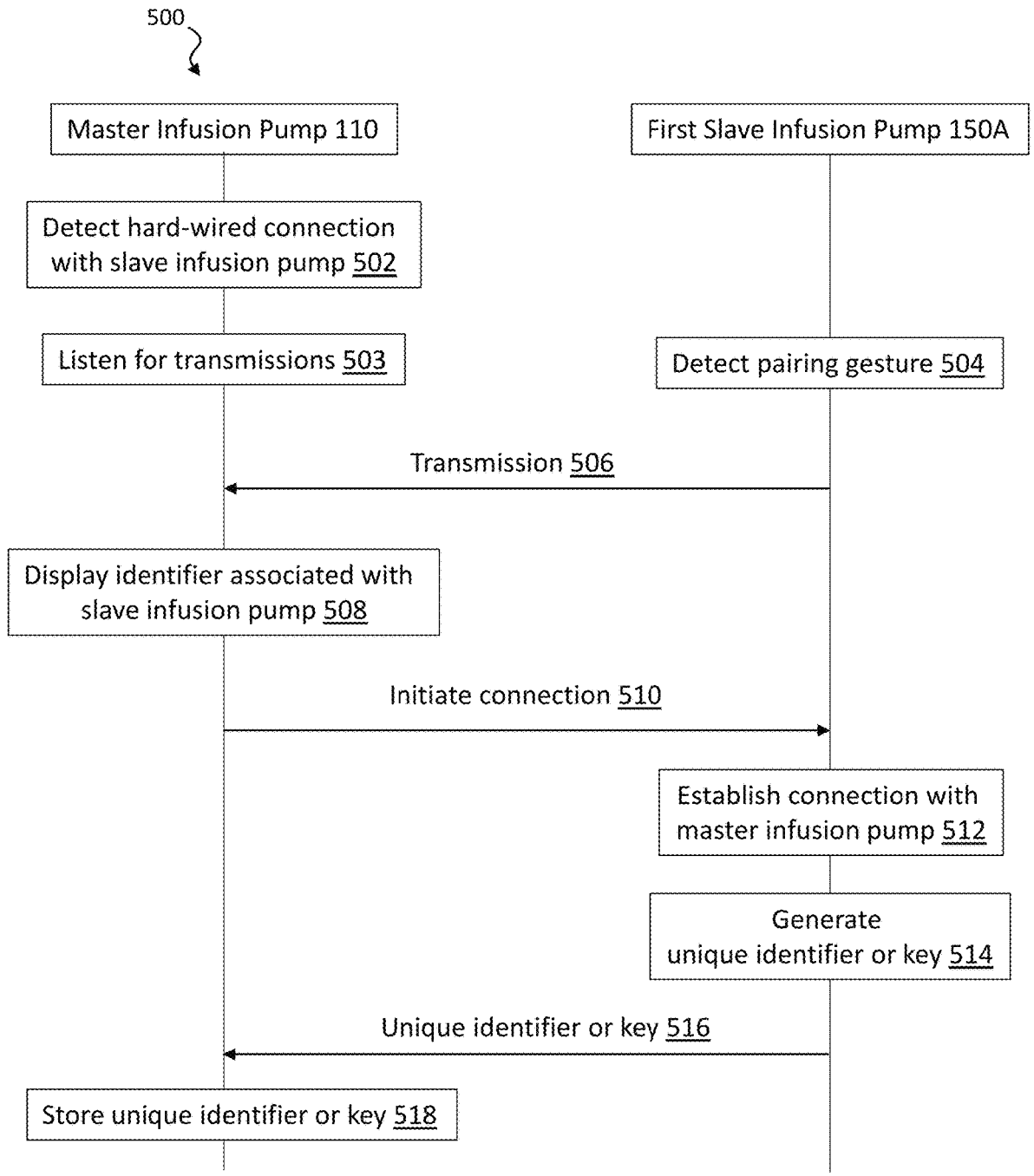
FIG. 5 depicts a pairing process associated with communications between a master infusion pump and a slave infusion pump, in accordance with some example embodiments.

FIG. 5 illustrates an example of a pairing process 500 between the master infusion pump 110 and/or the app and the first, second, and third slave infusion pumps 150A, 150B, 150C. During an initial pairing and/or binding process (e.g., as described with respect to FIG. 5), the master infusion pump 110 and/or the app and the first, second, and third slave infusion pumps 150A, 150B, 150C may be paired. The initial pairing may be performed, for example, when the slave infusion pumps 150A, 150B, 150C are ready to be configured for use by a user. The clinician, may perform the initial pairing in a medical facility, such as in the patient care room. After the initial pairing, the user may, with the first, second, and/or third slave infusion pump 150A, 150B, 150C and/or the app, move to a remote location, such as to the user's home for delivery of the fluid to the user.

Upon completion of the initial pairing, the master infusion pump 110 may become disconnected from the first, second, and third slave infusion pumps 150A, 150B, 150C. The first, second, and third slave infusion pumps 150A, 150B, 150C may be turned off, the master infusion pump 110 may be turned off, the first, second, and third slave infusion pumps 150A, 150B, 150C may move out of radio range of the master infusion pump 110, and/or the like.

While the pairing process 500 is described with respect to the first slave infusion pump 150A, the pairing process may also be used to pair the master infusion pump 110 and/or the app with any of the slave infusion pumps 150, including the second infusion pump 150B and the third slave infusion pump 150C. Additionally, and/or alternatively, while the pairing process 500 is described with respect to pairing the master infusion pump 110 with first slave infusion pump 150, the same or similar process may be used to pair the app (or user device 130) with the first slave infusion pump 150. To pair the master infusion pump 110 with the first slave infusion pump 150A, the first slave infusion pump 150A may first be connected to the master infusion pump 110 via a wired connection. For example, at 502, the master infusion pump 110 may detect a hard-wired connection between the first slave infusion pump 150A and the master infusion pump 110. In response to detecting the hard-wired connection between the first slave infusion pump 150A and the master infusion pump 110, the master infusion pump 110 may begin listening for transmissions from the first slave infusion pump 150A, at 503.

Additionally and/or alternatively, the master infusion pump 110 may detect a request to enter a pairing and/or engineering mode, which causes the master infusion pump 110 to begin listening for transmissions from the first slave infusion pump 150A. The request to enter the pairing mode may include a selection of a menu item via a user interface of the master infusion pump 110, selection of a button on the master infusion pump 110, and/or the like. In response to detecting the request to enter the pairing and/or engineering mode, alone, or in combination with detecting the hard-wired connection between the first slave infusion pump 150A and the master infusion pump 110, the master infusion pump 110 may begin listening for transmissions from the first slave infusion pump 150A.

At 504, the first slave infusion pump 150A may detect a pairing gesture, such as a clinician's interaction with a pairing button 156 on the first slave infusion pump 150A. The pairing gesture may be performed by the clinician 165 by interacting with a control element or feature, such as depressing a button, on the first slave infusion pump 150A within a predetermined time (e.g., 0.25 seconds, 0.5 seconds, 0.75 seconds, 1 second, 2 seconds, 2.25 seconds, 2.5 seconds, 2.75 seconds, 3 seconds, 3.25 seconds, 3.5 seconds, 3.75 seconds, 4 seconds, 4.25 seconds, 4.5 seconds, 4.75 seconds, 5 seconds, 5.25 seconds, 5.5 seconds, 5.75 seconds, 6 seconds, or more, and other predetermined time intervals).

At 506, the first slave infusion pump 150A may wirelessly transmit (as a broadcast or multi-cast, for example) one or more transmissions, such as via Bluetooth Low Energy, or other wireless technology. The broadcast of the transmission allows the first slave infusion pump 150A to be discovered by another device, such as the master infusion pump 110. The transmission may include identifying data associated with the first slave infusion pump 150A, the clinician, and/or the user, such as an identifier associated with the first slave infusion pump 150A.

At 508, in response to receiving the transmission, the master infusion pump 110 may display the identifier associated with the first slave infusion pump 150A. In some implementations, the master infusion pump 110 displays one or more identifiers associated with the slave infusion pumps 150 that are broadcasting transmissions. The master infusion pump 110 may receive, via the user interface of the master infusion pump 110, a selection of the first slave infusion pump 150A from the slave infusion pumps being displayed by the master infusion pump 110. In response to receiving the transmission from the first slave infusion pump 150A the master infusion pump 110 may determine to initiate a connection to the first slave infusion pump 150A. This determination may be based on the selection of the first slave infusion pump 150A via the master infusion pump 110 and/or the contents of the transmission (e.g., the identifying data contained in the transmission or other data in the transmission). The master infusion pump 110 may determine that the transmission includes a serial number, a model number, manufacturer-specific data, and/or other information associated with the first slave infusion pump 150A that the master infusion pump 110 recognizes as conforming to an expected format, value, and/or range of values. The master infusion pump 110 may include a memory device to store at least some of the identifying data included in the transmission. For example, if the transmission includes a device identifier, the master infusion pump 110 may locally store the device serial number.

At 510, the master infusion pump 110 may initiate establishment of a connection with the first slave infusion pump 150A. In response to determining to connect (e.g., pair) with the master infusion pump 110 may initiate connection establishment by at least sending a connection request message to the first slave infusion pump 150A.

At 512, the first slave infusion pump 150A and the master infusion pump 110 may establish a connection. For example, the master infusion pump 110 may send one or more messages during a pairing process, such as Bluetooth pairing request messages. In response, the first slave infusion pump 150A may send one or more messages, such as Bluetooth pairing response messages. The first slave infusion pump 150A may display an indicator, such as via the visual indicator on the first slave infusion pump 150A to indicate an established connection.

At 514, the first slave infusion pump 150A may generate a unique identifier and/or key. The unique identifier and/or key may be of any length, including 2 bits, 4 bits, 8 bits, 16 bits, 32 bits, 64 bits, or longer. The unique identifier and/or key may be used for encryption and decryption of wireless messages and/or the contents thereof sent by the first slave infusion pump 150A and the master infusion pump 110. As such, the unique identifier and/or key may be used to mask identifying information found in transmissions sent by the first slave infusion pump 150A and the master infusion pump 110. At 516, the first slave infusion pump 150A may transmit the unique identifier and/or key to the master infusion pump 110.

At 518, the master infusion pump 110 may store the unique identifier and/or key. Storing the unique identifier and/or the key may allow the master infusion pump 110 to continue to send and/or receive transmission to and/or from the first slave infusion pump 150A. Accordingly, the master infusion pump 110 may securely transmit a desired fluid delivery protocol to the first slave infusion pump 150A and/or the master infusion pump 110 may securely receive one or more logged parameters associated with the delivery of the fluid therapy from the first slave infusion pump 150A.

Referring back to FIG. 2, once the master infusion pump 110 and/or the app, and the first slave infusion pump 150A have been securely paired, the master infusion pump 110 may transmit the fluid delivery protocol to the first slave infusion pump 150A. The master infusion pump 110 and/or the app may then pair with the second slave infusion pump 150B and/or the third slave infusion pump 150C and transmit a fluid delivery protocol to the second slave infusion pump 150B and/or the third slave infusion pump 150C.

In some implementations, after the slave infusion pump 150 receives the desired fluid delivery protocol, the slave infusion pump 150 may be used to deliver the fluid to the user based on the fluid delivery protocol. As described herein, the slave infusion pump 150 may be used to deliver the fluid to the user at the medical facility and/or at locations remote from the medical facility, such as at the user's home and/or while the user is travelling.

The slave infusion pump 150 (e.g., the first, second, and/or third slave infusion pump 150A, 150B, 150C) may measure and/or log one or more parameters based on the fluid delivery protocol and/or the delivery of the fluid to the user. For example, the slave infusion pump 150 may measure and/or log one or more parameters, such as the time of the fluid delivery, the user's information, the number of fluid deliveries, the volume of fluid delivered, the type of fluid being delivered, the volume of the fluid remaining to be delivered, an identifier of the master infusion pump from which the slave infusion pump received the fluid delivery protocol, location data, and/or the like. The slave infusion pump 150 may wirelessly transmit the measured and/or logged parameters to the user device 130 (e.g., to the app). In some implementations, at least one of the measured and/or logged parameters may be displayed to the user via the user device 130. In some implementations, at least one of the measured and/or logged parameters may be transmitted from the user device 130 to the master infusion pump 110 and/or directly to the server 126 to be stored in one or more of the data systems 125 described herein. Such configurations allow the slave infusion pump 150 to be used at locations away from the medical facility, and still update the clinicians at the medical facility and/or the records associated with the delivery of the fluid therapy to the user.

In some implementations, the slave infusion pump 150 may detect an error. The error may be associated with operation of the slave infusion pump 150 and/or with the delivery of the fluid to the user. For example, the slave infusion pump 150 may detect a low battery, an occlusion in the fluid delivery line, a disconnection of the fluid delivery line from the user, a low volume of fluid remaining to be delivered, a malfunctioning component of the slave infusion pump 150, and/or the like. In response to detecting the error, the slave infusion pump 150 may display a visual (e.g., light, colored light such as a red, orange, yellow, or green light, a patterned light, and the like) and/or audio (e.g., sound, patterned sound, and the like) feedback via one or more of the indicators on the slave infusion pump 150. Additionally and/or alternatively, the slave infusion pump 150 may transmit the error and/or details relating to the error to the user device 130. The user device 130 (e.g., the app) may present, via the display of the user device 130, the details associated with the error, to the user. The details relating to the error may include the type of error that has occurred, instructions for correcting the error, and/or instructions to contact the clinician. In some implementations, the user device 130 may contact the clinician in response to receiving the error and/or details associated with the error from the slave infusion pump 150. For example, if the user device 130 is implemented as a smartphone, the details related to the error may cause the smartphone to initiate a communication session (e.g., chat, telephone call, voice over IP call, video call, etc.) with a device associated with the clinician.

In some implementations, in response to detection of the error, the slave infusion pump 150 may stop delivery of the fluid to the user, for example, until the error is resolved (e.g., when the slave infusion pump receives instructions to continue delivering the fluid). Additionally and/or alternatively, the user device 130 may cause the slave infusion pump 150 to stop delivering the fluid to the user in response to receiving the error and/or details associated with the error from the slave infusion pump 150. In some implementations, the user device 130 may cause the slave infusion pump 150 to stop delivering the fluid to the user based on the type of error received from the slave infusion pump 150. For example, if the user device 130 determines that the fluid delivery line is disconnected from the user and/or the fluid delivery line is occluded, the user device 130 may cause the slave infusion pump 150 to sop delivering the fluid to the user. This allows for the slave infusion pump 150 to be used at locations remote from the medical facility and improves the portability and usability of the slave infusion pump 150 away from the medical facility.

In some implementations, the slave infusion pump 150 may include various power modes to conserve power consumption. For example, the slave infusion pump 150 may include a sleep mode in which the slave infusion pump 150 enters the sleep mode if it is not used within a predetermined period of time (e.g., 15 minutes, 30 minutes, 45 minutes, 60 minutes, 120 minutes, and/or the like). In some implementations, the slave infusion pump 150 may include a communication mode in which the slave infusion pump 150 transmits the one or more parameters to the user device 130 continuously and/or at predetermined time intervals (e.g., every 15 minutes, 30 minutes, 45 minutes, 60 minutes, 120 minutes, and/or the like). In some implementations, the slave infusion pump 150 may include a programming mode in which the slave infusion pump only broadcasts transmissions while in communication with and/or when attempting to communicate with the master infusion pump 110. In some implementations, to conserve power, the slave infusion pump 150 may only communicate directly with the master infusion pump 110 when communications (e.g., the pairing) is initiated by the master infusion pump 110.

FIG. 6 schematically illustrates another example of the infusion management system 100 consistent with implementations of the current subject matter. The infusion management system 100 may include one or more of the features of the infusion management system 100 described herein and illustrated in FIGS. 1-5 and 7-9C, such as the server 126, the master infusion pump 110, the user device 130 including the app, and one or more slave infusion pumps 150.

For example, the infusion management system 100 includes one or more local edge devices, such as the user device 130, the master infusion pump 110, and/or the one or more slave or ambulatory infusion pumps 150, one or more applications and services, cloud storage (e.g., such as via the data system 125), and secure application programming interfaces (APIs) and communication protocols (e.g., such as at the data system 125 and/or the server 126), to allow for seamless patient care workflows. The one or more applications and services may include an active directory, message services 658, provisioning services 656, device adapters 654, and/or the like.

As shown in FIG. 6, the infusion management system 100 uses cross-operating system deployment to maximize supported devices (e.g., the user device 130 and/or the one or more slave infusion pumps 150). As described herein, the user device 130 may include an app for communicating with the one or more slave infusion pumps 150. Communications between the app and the one or more slave infusion pumps 150 may be supported through standard and secure Bluetooth Low Energy, or other wireless technology, such as Wi-Fi (e.g., with cellular connectivity). The wireless technology may leverage x509 certificates. Consistent with implementations of the current subject matter, the stored data (e.g., data at rest) may be secured with AES-256 encryption. In some implementations, the app may receive alarm notifications, associate a patient (e.g., the user 160) to a pump (e.g., the slave infusion pump 150), and/or program (e.g., send at least one fluid delivery protocol, pause delivery of the fluid, resume delivery of the fluid, and/or the like) and collect information from the slave infusion pump 150.

Referring to FIG. 6, the infusion management system 100 may include one or more web-based applications 660. The one or more web-based applications 660 provide end-to-end support for fluid delivery, such as from manufacture of the fluid to delivery of the fluid to the user and/or to disposal of wasted fluid. The one or more web-based applications may allow for configuration of fluid libraries, device provisioning, and/or device updating, such as via over-the-air firmware updates.

Consistent with implementations of the current subject matter, the infusion management system 100 may additionally and/or alternatively provide and manage data storage, such as via the data system 125 and/or server 126. For example, the infusion management system 100 may integrate various system endpoints and provide secure, standards compliant (e.g., Health Insurance Portability and Accountability Act-compliant) data storage and management.

Consistent with implementations of the current subject matter, the infusion management system 100 may additionally and/or alternatively include one or more APIs and communication protocols, such as an infusion pump platform API 650, an authorization API 652, and/or the like. This allows for secure communications between the server 126 and/or the data system 125 with the master infusion pump 110, the one or more slave infusion pumps 150, and/or the user device 130. This also provides a seamless interface between the server 126 and/or the data system 125, the master infusion pump 110, the one or more slave infusion pumps 150, and/or the user device 130.

Additionally, and/or alternatively, the infusion management system 100 may include one or more cellular communications features, such as via the network 105. The one or more cellular communications features may include General Packet Radio Services (GPRS), Long-Term Evolution (LTE) networks, 5G cellular technology, and/or the like. Such cellular communications features may increase system mobility and deployment options.

Figure 7:
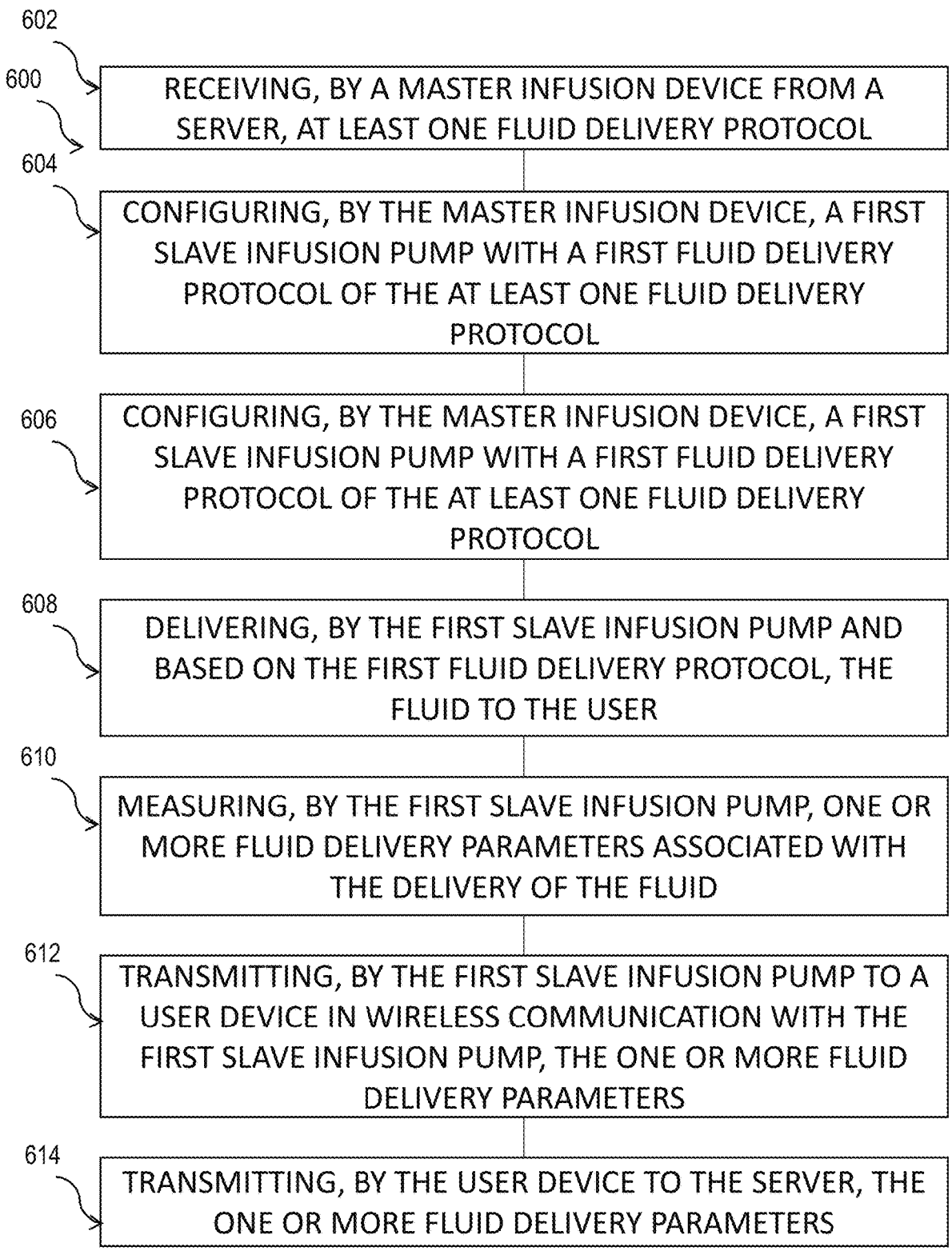
FIG. 7 depicts a flowchart illustrating a process for configuring a slave infusion pump, in accordance with some example embodiments.

FIG. 7 illustrates an example process 600 for configuring one or more slave infusion pumps via a single interface, with the infusion management system consistent with implementations of the current subject matter. Consistent with implementations of the current subject matter, the infusion management system may reduce the amount of space pumps occupy in a medical facility, allow the pumps to be located closer to the infusion site on the patient's body to provide more accurate measurements and reduce the likelihood that the pumps will be disconnected from the patient, improve the portability of the pumps to allow patients to more comfortably use the pumps away from the medical facility, decrease the cost of manufacturing the pumps, and/or enhance the security of communications between the slave infusion pump and master infusion pump.

At 602, the master infusion device (e.g., the master infusion pump 110 and/or the user device 130 such as the app) may receive, from a server (e.g., the server 126), at least one fluid delivery protocol. The fluid delivery protocol may include one or more parameters for delivering a fluid to a user. For example, the one or more parameters may include a volume of fluid to be delivered to the user, a type of fluid to be delivered to the user, a time interval of fluid delivery, a frequency of fluid delivery, a delivery rate at which the fluid is to be delivered to the user, and/or the like.

In some implementations, the master infusion device receives a selection by a clinician or other authorized individual, via a user interface of the master infusion device, of the desired fluid delivery protocol. In some implementations, the master infusion device may include one or more authentication features to allow the clinician access to the server 126, and to prevent the user from accessing the server 126. For example, the authentication features may include a user name and password, a badge scan, a fingerprint scan or a retina scan, and/or the use of facial recognition to identify the clinician, to provide access, via the master infusion device, to retrieve and/or alter one or more aspects of the fluid delivery protocols from the server 126. Such configurations help to ensure that the user is not able to retrieve and/or alter one or more aspects of the fluid delivery protocols and that the clinician is permitted to access and/or alter one or more aspects of the fluid delivery protocols.

At 604, the master infusion device may configure a first slave infusion pump (e.g., at least one of the slave infusion pumps 150, such as the first slave infusion pump 150A) with a first fluid delivery protocol of the at least one fluid delivery protocol. For example, the master infusion device may transmit the first fluid delivery protocol to the first slave infusion pump. As described above with respect to pairing process 500 illustrated in FIG. 5, the master infusion device may be securely paired with the first slave infusion pump to establish a secure communication channel for transmitting the first fluid delivery protocol from the master infusion device to the first slave infusion pump and/or for transmitting logged and/or measured parameters of the fluid delivery from the first slave infusion pump to the master infusion device. In some implementations, as described herein, the first slave infusion pump may be connected to the master infusion device via a hard-wired and/or wireless connection to establish the secure communication channel.

At 606, the master infusion device may configure a second slave infusion pump (e.g., at least one of the slave infusion pumps 150, such as the second slave infusion pump 150B) with a second fluid delivery protocol of the at least one fluid delivery protocol. For example, the master infusion device may transmit the second fluid delivery protocol to the second slave infusion pump. As described above with respect to pairing process 500 illustrated in FIG. 5, the master infusion device may be securely paired with the second slave infusion pump to establish a secure communication channel for transmitting the second fluid delivery protocol from the master infusion device to the second slave infusion pump and/or for transmitting logged and/or measured parameters of the fluid delivery from the second slave infusion pump to the master infusion device. In some implementations, as described herein, the second slave infusion pump may be connected to the master infusion device via a hard-wired and/or wireless connection to establish the secure communication channel.

The first and second fluid delivery protocols may be the same or different, depending on the user, the type of fluid to be delivered to the user, the volume of fluid to be delivered to the user, the delivery rate of the fluid to be delivered to the user, the frequency of delivery of the fluid, the time intervals for delivering the fluid, and/or the like.

In some implementations, the first fluid delivery protocol may be delivered by the first slave infusion pump to a first user and the second fluid delivery protocol may be delivered by the second slave infusion pump to a second user. Alternatively, the first fluid delivery protocol and the second fluid delivery protocol may be delivered by the first and second slave infusion pumps, respectively, in situations, such as when multiple types of fluids may be delivered to the user.

As described above, with respect to at least FIGS. 1, 2, 3A, and 3B, the first slave infusion pump and/or the second slave infusion pump may include limited functionality. For example, the first slave infusion pump and/or the second slave infusion pump may include an indicator for providing visual and/or audio feedback to the user based on one or more operations of the first slave infusion pump and/or the second slave infusion pump. The indicator may display a light, change a light color, change a light pattern, flash a light, play a sound, play a sound pattern, and/or the like, when an error occurs in the delivery of the fluid to the user. The error may indicate an occlusion in the fluid delivery line, an interruption in the connection between the fluid delivery line and the user, a low battery of the slave infusion pump, a low volume of fluid to be delivered to the user and/or the like. The first slave infusion pump and/or the second slave infusion pump may also include a button for powering the first slave infusion pump and/or the second slave infusion pump on or off. In some implementations, the first slave infusion pump and/or the second slave infusion pump does not include a display for displaying information related to the delivery of the fluid to the user. Instead, in some implementations, the first slave infusion pump and/or the second slave infusion pump may wirelessly communicate with a user device to display the information related to the delivery of the fluid to the user. Such configurations help the first slave infusion pump and/or the second slave infusion pump maintain a reduced profile to improve portability and may allow for the first slave infusion pump and/or the second slave infusion pump to be carried and/or worn by the user.

At 608, the fluid may be delivered, based on the first fluid delivery protocol, by the first slave infusion pump to the user. For example, the first slave infusion pump may deliver the fluid to the user based on the fluid delivery rate, the time intervals, and/or the like stored as part of the first fluid delivery protocol. In some implementations, the fluid may be delivered, based on the second fluid delivery protocol, by the second slave infusion pump to the user. For example, the second slave infusion pump may deliver the fluid to the user based on the fluid delivery rate, the time intervals, and/or the like stored as part of the second fluid delivery protocol.

At 610, the first slave infusion pump may measure and/or log one or more fluid delivery parameters associated with the delivery of the fluid by the first slave infusion pump. For example, the first slave infusion pump may measure and/or log the time of the fluid delivery, the user's information, the number of fluid deliveries, the volume of fluid delivered, the type of fluid being delivered, the volume of the fluid remaining to be delivered, an identifier of the master infusion device from which the slave infusion pump received the fluid delivery protocol, location data, and/or the like. Similarly, the second slave infusion pump may measure and/or log one or more fluid delivery parameters associated with the delivery of the fluid by the second slave infusion pump.

At 612, the first slave infusion pump and/or the second slave infusion pump may transmit the measured and/or logged fluid delivery parameters associated with the delivery of the fluid to the user device for display to the user. In some implementations, the user device (e.g., via an app) displays at least one of the measured and/or logged fluid delivery parameters to the user. In some implementations, the first slave infusion pump and/or the second slave infusion pump may detect an error. In response to detecting the error, the first slave infusion pump and/or the second slave infusion pump may provide visual and/or audio feedback to the user via the indicator on the first slave infusion pump and/or the second slave infusion pump, and/or transmit the error to the user device. The user device may then display the error and/or information associated with the error to the user. In some implementations, the first slave infusion pump and/or the second slave infusion pump stops the delivery of the fluid to the user in response to detecting the error.

At 614, the user device may transmit at least one of the measured and/or logged parameters associated with the delivery of the fluid to the server (e.g., directly to the server). The transmitted measured and/or logged parameters may be used by the server to update one or more medical records of the user, and/or to alert the clinician at the medical facility. Such configurations help to improve the ability for the user to use the slave infusion pumps described herein at locations away from the medical facility and help to improve the portability of the slave infusion pumps.

Figure 8:
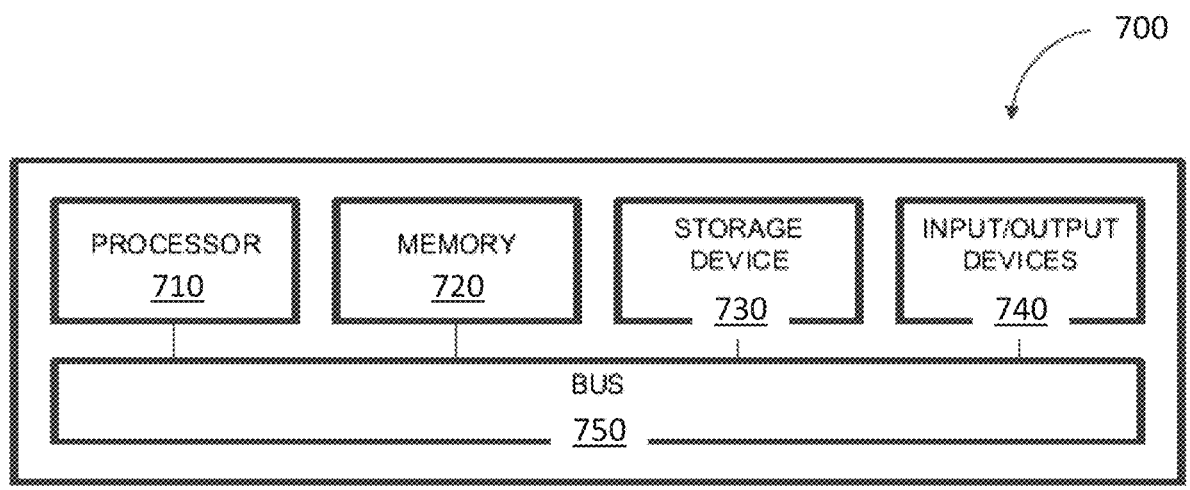
FIG. 8 depicts a block diagram illustrating a computing system, in accordance with some example embodiments.

FIG. 8 depicts a block diagram illustrating a computing system 700 consistent with implementations of the current subject matter. Referring to FIGS. 1 and 7, the computing system 700 can be used to implement the master infusion pump 110, the slave infusion pump 150, the data systems 125, the server 126, the user device 130, the display 154, and/or any components therein.

As shown in FIG. 8, the computing system 700 can include a processor 710, a memory 720, a storage device 730, and input/output devices 740. The processor 710, the memory 720, the storage device 730, and the input/output devices 740 can be interconnected via a system bus 750. The processor 710 is capable of processing instructions for execution within the computing system 700. Such executed instructions can implement one or more components of, for example, the master infusion pump 110 and/or the slave infusion pump 150. In some example embodiments, the processor 710 can be a single-threaded processor. Alternatively, the processor 710 can be a multi-threaded processor. The processor 710 is capable of processing instructions stored in the memory 720 and/or on the storage device 730 to present graphical information for a user interface provided via the input/output device 740.

The memory 720 is a computer readable medium such as volatile or non-volatile that stores information within the computing system 700. The memory 720 can store data structures representing configuration object databases, for example. The storage device 730 is capable of providing persistent storage for the computing system 700. The storage device 730 can be a floppy disk device, a hard disk device, an optical disk device, or a tape device, or other suitable persistent storage means. The input/output device 740 provides input/output operations for the computing system 700. In some example embodiments, the input/output device 740 includes a keyboard and/or pointing device. In various implementations, the input/output device 740 includes a display unit for displaying graphical user interfaces.

According to some example embodiments, the input/output device 740 can provide input/output operations for a network device. For example, the input/output device 740 can include Ethernet ports or other networking ports to communicate with one or more wired and/or wireless networks (e.g., a local area network (LAN), a wide area network (WAN), the Internet).

In some example embodiments, the computing system 700 can be used to execute various interactive computer software applications that can be used for organization, analysis and/or storage of data in various formats. Alternatively, the computing system 700 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 740. The user interface can be generated and presented to a user by the computing system 700 (e.g., on a computer screen monitor, etc.).

Figure 9A:
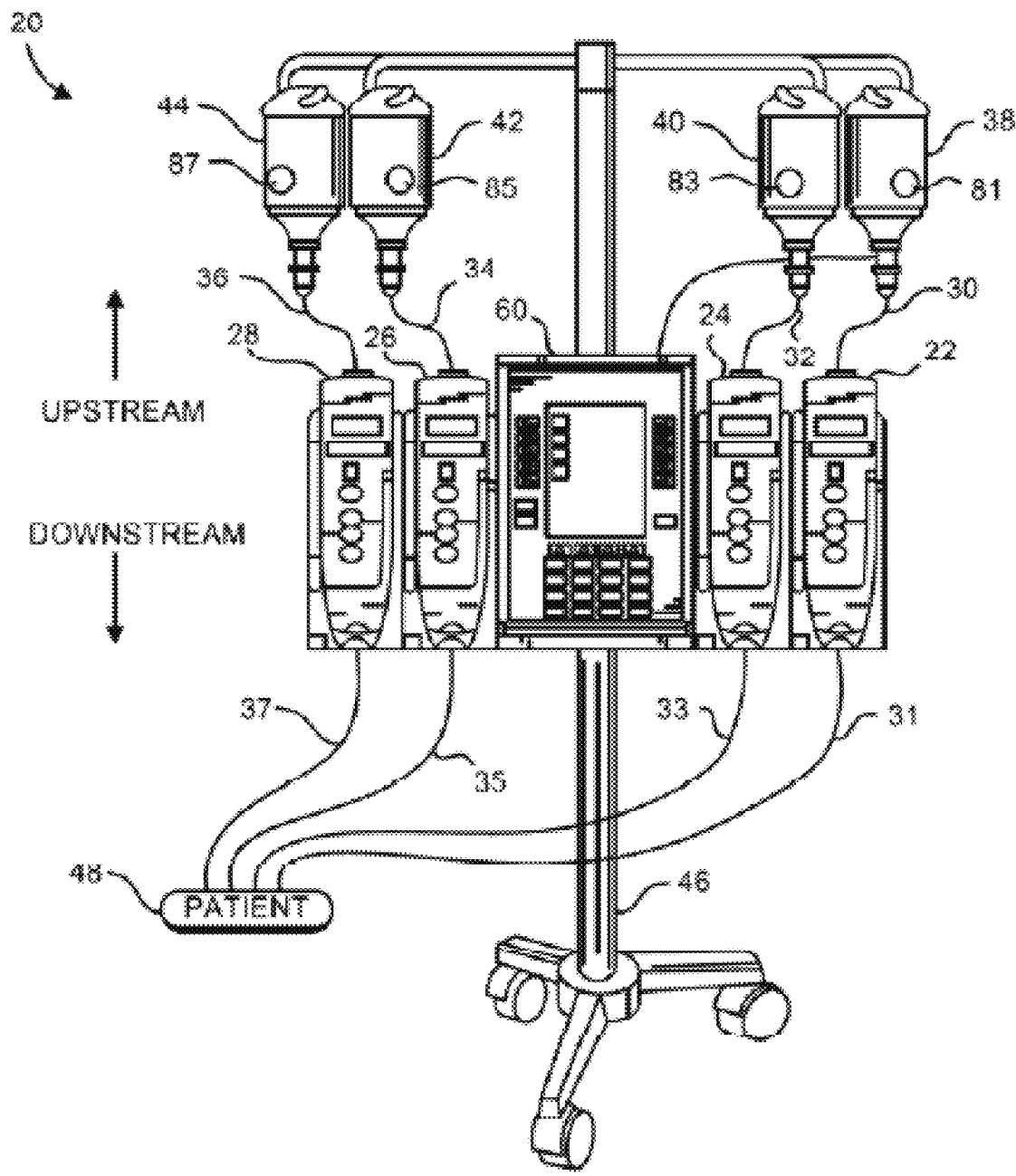
FIG. 9A depicts a front view of a patient care system, in accordance with some example embodiments.
Figure 9B:
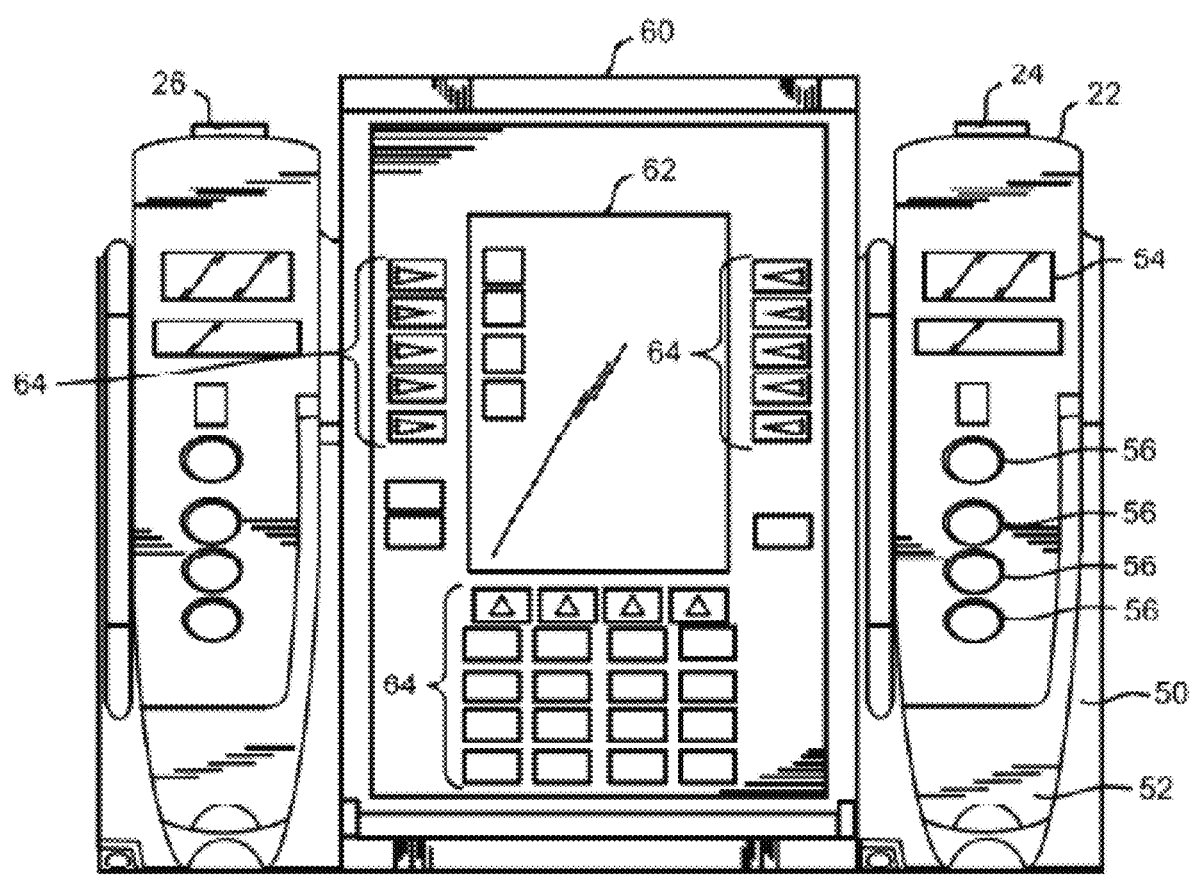
FIG. 9B depicts an enlarged view of a portion of a patient care system, in accordance with some example embodiments.
Figure 9C:
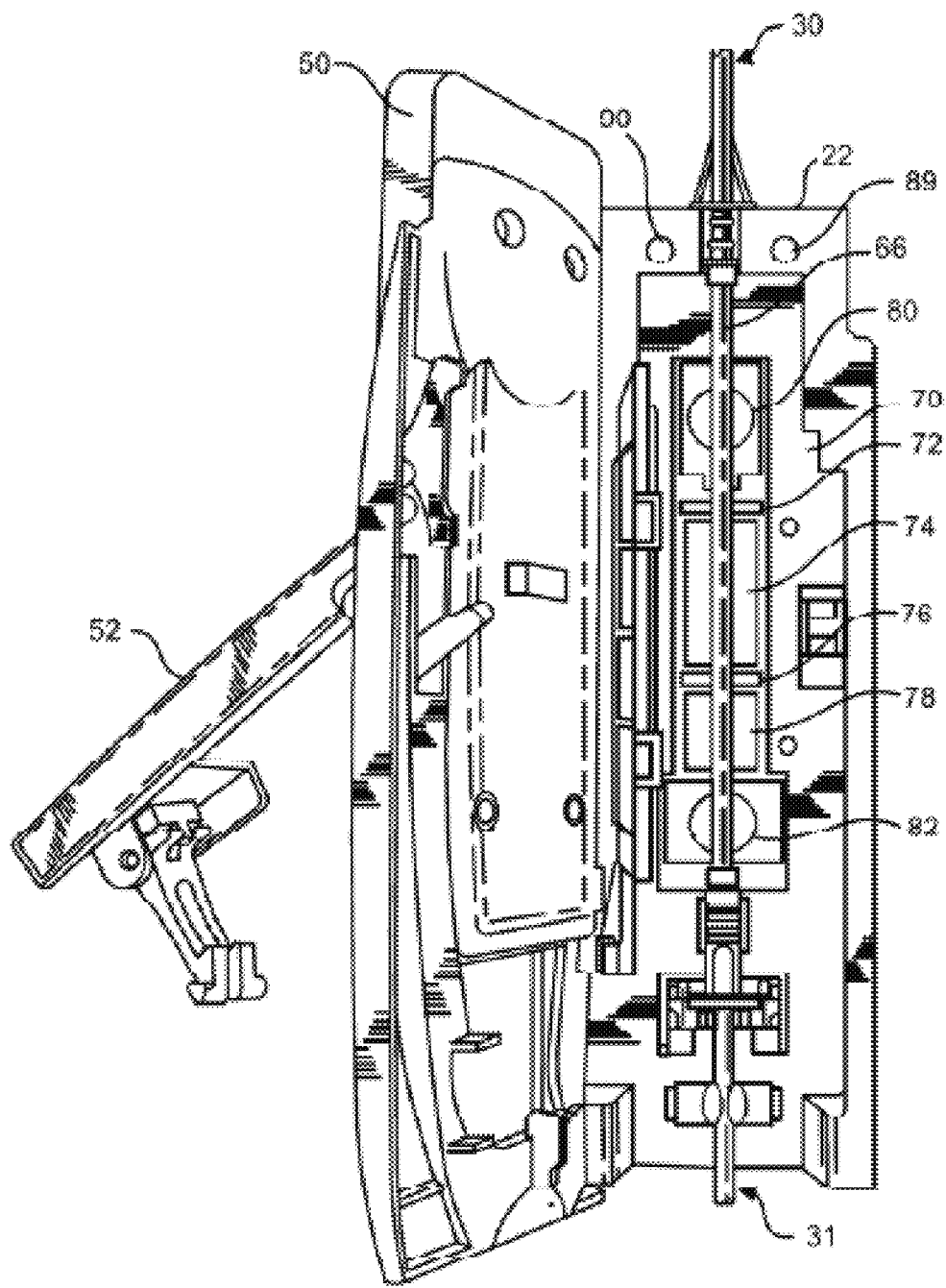
FIG. 9C depicts a perspective view of a pump, in accordance with some example embodiments.

In some example embodiments, a pump 22 (e.g., the master infusion pump 110 and/or the slave infusion pump 150) may be part of a patient care system 20. FIGS. 9A-9C illustrate example embodiments of the patient care system 20, though other types of patient care systems may be implemented. Referring to FIG. 9A, the patient care system 20 may include the pump 22 as well as additional pumps 24, 26, and 28. Although a large volume pump (LVP) is illustrated, other types of pumps may be implemented, such as a small volume pump (SVP), a TCI pump, a syringe pump, an anesthesia delivery pump, and/or a patient-controlled analgesic (PCA) pump configured to deliver a medication to a patient in accordance with one or more fluid delivery protocols. In some implementations, the slave infusion pumps 150 described herein may be communicatively coupled with and/or form a part of the pumps 22, 24, 26, 28. The pump 22 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 22 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like.

As shown in FIG. 9A, each of the pump 22, 24, 26, and 28 may be fluidly connected with an upstream fluid line 30, 32, 34, and 36, respectively. Moreover, each of the four pumps 22, 24, 26, and 28 may also fluidly connected with a downstream fluid line 31, 33, 35, and 37, respectively. The fluid lines can be any type of fluid conduit, such as tubing, through which fluid can flow. At least a portion of one or more of the fluid lines may be constructed with a multi-layered configuration as described herein.

Fluid supplies 38, 40, 42, and 44, which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 22, 24, 26, and 28 may be used to infuse each of the fluids of the fluid supplies into the patient. The pumps 22, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 9A. Many have check valves, drip chambers, valved ports, connectors, and other devices well known to those skilled in the art. These other devices have not been included in the drawings so as to preserve clarity of illustration. In addition, it should be noted that the drawing of FIG. 9A is not to scale and that distances have been compressed for the purpose of clarity. In an actual setting, the distance between the bottles 38, 40, 42, and 44 and the pump modules 22, 24, 26, and 28 could be much greater.

Referring now to FIG. 9B, an enlarged view of the front of the patient care system 20 is shown. The pump 22 may include a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 9C. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). The display 54 may otherwise be a part of or be coupled to the pump 22. Control keys 56 exist for programming and controlling operations of the pump as desired. The pump 22 also includes audio alarm equipment in the form of a speaker (not shown).

In the embodiment shown, a programming module 60 is attached to the left side of the pump 22. In some embodiments, the programming module 60 forms a part of the pump 22. Other devices or modules, including another pump, may be attached to the right side of the pump 22, as shown in FIG. 9A. In such a system, each attached pump represents a pump channel of the overall patient care system 20. In one embodiment, the programming module is used to provide an interface between the pump 22 and external devices as well as to provide most of the operator interface for the pump 22.

The programming module 60 includes a display 62 for visually communicating various information, such as the operating parameters of the pump 22 and alert indications and alarm messages. In some implementations, the display 62 forms a part of the master infusion pump 110 and/or the user device 130. The programming module 60 may additionally and/or alternatively display the one or more patient parameters and the corresponding values for each of the one or more patient parameters described herein to the display 54 and/or the display 64. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump. In some embodiments, the pump 22 may communicate with a server (e.g., the server 126) and/or one or more slave infusion pumps 150 to transmit one or more fluid delivery protocols to the one or more slave infusion pumps 150.

The communications system may take the form of a radio frequency ("RF") (radio frequency) system, an optical system such as infrared, a Blue Tooth system, or other wired or wireless system. The bar code scanner and communications system may alternatively be included integrally with the pump 22, such as in cases where a programming module is not used, or in addition to one with the programming module. Further, information input devices need not be hard-wired to medical instruments, information may be transferred through a wireless connection as well.

FIG. 9B includes a second pump 26 connected to the programming module 60. As shown in FIG. 9A, more pump modules may be connected. Additionally, other types of modules may be connected to the pump modules or to the programming module. The programming module may maintain determine, adjust, and/or display values (e.g., default values) of each of the one or more patient parameters for each pump (e.g., pump 22 and pump 26).

Turning now to FIG. 9C, the pump 22 is shown in perspective view with the front door 50 open, showing the upstream fluid line 30 and downstream fluid line 31 in operative engagement with the pump 22. The pump 22 directly acts on a tube 66 (also referred to as a pump segment) that connects the upstream fluid line 30 to the downstream fluid line 31 to form a continuous fluid conduit, extending from the respective fluid supply 38 (FIG. 9A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 9C further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 9A) and the flow control device, so that the connection of the correct fluid supply with the correct pump may be verified before any fluid is pumped to the patient.

With reference still to FIG. 9C, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 9A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

Although the disclosure, including the figures, described herein may describe and/or exemplify different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise" and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infrared transmission channels as well as a network connection to another computer or networked device, and the internet or including email transmissions and information recorded on websites and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system, comprising:
   at least one data processor; and
   at least one memory storing instructions which, when executed by the at least one data processor, the at least one data processor is configured to result in operations comprising:
   receiving, by a master infusion device from a server, at least one fluid delivery protocol, the at least one fluid delivery protocol comprising one or more parameters for delivering a fluid to a user;
   configuring, by the master infusion device, a first slave infusion pump with a first fluid delivery protocol of the at least one fluid delivery protocol;
   configuring, by the master infusion device, a second slave infusion pump with a second fluid delivery protocol of the at least one fluid delivery protocol; and
   delivering, by the first slave infusion pump and based on the first fluid delivery protocol, the fluid to the user, wherein the first fluid delivery protocol is different from the second fluid delivery protocol, wherein the first slave infusion pump is configured to deliver the fluid to a first user based on the first fluid delivery protocol, and wherein the second slave infusion pump is configured to deliver the fluid to a second user based on the second fluid delivery protocol.

2. The system of claim 1, wherein the first slave infusion pump is communicatively coupled with a user device, the user device configured to display at least one of the one or more parameters for delivering the fluid to the user.

3. The system of claim 2, wherein the first slave infusion pump does not comprise a display.

4. The system of claim 1, wherein the operations further comprise:
   the first slave infusion pump configured to measure one or more fluid delivery parameters associated with the delivery of the fluid; and
   the first slave infusion pump configured to transmit to a user device in wireless communication with the first slave infusion pump, the one or more fluid delivery parameters.

5. The system of claim 1, wherein the receiving is configured to authenticate a clinician to provide access to the fluid delivery protocol on the server.

6. The system of claim 1, wherein the first slave infusion pump is configured to establish a secure connection between the first slave infusion pump and the master infusion device, the establishing comprising encrypting transmissions between the first slave infusion pump and the master infusion device.

7. The system of claim 1, wherein the operations further comprise:
   being configured to detect an error in the delivery of the fluid to the user; and
   being configured to stop the delivery of the fluid to the user.

8. The system of claim 7, wherein the operations further comprise:
   being configured to transmit the error to a user device in wireless communication with the first slave infusion pump; and
   display information associated with the error via the user device.

9. A method, comprising:
   receiving, by a master infusion device from a server, at least one fluid delivery protocol, the at least one fluid delivery protocol comprising one or more parameters for delivering a fluid to a user;
   configuring, by the master infusion device, a first slave infusion pump with a first fluid delivery protocol of the at least one fluid delivery protocol;
   configuring, by the master infusion device, a second slave infusion pump with a second fluid delivery protocol of the at least one fluid delivery protocol; and
   delivering, by the first slave infusion pump and based on the first fluid delivery protocol, the fluid to the user, wherein the first fluid delivery protocol is different from the second fluid delivery protocol, wherein the first slave infusion pump is configured to deliver the fluid to a first user based on the first fluid delivery protocol, and wherein the second slave infusion pump is configured to deliver the fluid to a second user based on the second fluid delivery protocol.

10. The method of claim 9, wherein the first slave infusion pump is communicatively coupled with a user device, the user device configured to display at least one of the one or more parameters for delivering the fluid to the user.

11. The method of claim 10, wherein the first slave infusion pump does not comprise a display.

12. The method of claim 9, further comprising:
    measuring, by the first slave infusion pump, one or more fluid delivery parameters associated with the delivery of the fluid; and transmitting, by the first slave infusion pump to a user device in wireless communication with the first slave infusion pump, the one or more fluid delivery parameters.

13. The method of claim 9, wherein the receiving further comprises authenticating a clinician to provide access to the fluid delivery protocol on the server.

14. The method of claim 9, wherein the configuring the first slave infusion pump comprises establishing a secure connection between the first slave infusion pump and the master infusion device, the establishing comprising encrypting transmissions between the first slave infusion pump and the master infusion device.

15. The method of claim 9, further comprising:
detecting an error in the delivery of the fluid to the user; and
stopping the delivery of the fluid to the user.

16. The method of any of claim 15, further comprising:
transmitting the error to a user device in wireless communication with the first slave infusion pump; and
displaying information associated with the error via the user device.

17. A non-transitory computer-readable storage medium including program code, which when executed by at least one data processor configured to perform operations comprising:
receiving, by a master infusion device from a server, at least one fluid delivery protocol, the at least one fluid delivery protocol comprising one or more parameters for delivering a fluid to a user;
configuring, by the master infusion device, a first slave infusion pump with a first fluid delivery protocol of the at least one fluid delivery protocol;
configuring, by the master infusion device, a second slave infusion pump with a second fluid delivery protocol of the at least one fluid delivery protocol; and delivering, by the first slave infusion pump and based on the first fluid delivery protocol, the fluid to the user, wherein the first fluid delivery protocol is different from the second fluid delivery protocol, wherein the first slave infusion pump is configured to deliver the fluid to a first user based on the first fluid delivery protocol, and wherein the second slave infusion pump is configured to deliver the fluid to a second user based on the second fluid delivery protocol.

18. The non-transitory computer-readable storage medium of claim 17 further including program code, which when executed by the at least one data processor, further configured to perform operations comprising:
measuring, by the first slave infusion pump, one or more fluid delivery parameters associated with the delivery of the fluid; and
transmitting, by the first slave infusion pump to a user device in wireless communication with the first slave infusion pump, the one or more fluid delivery parameters.

19. The non-transitory computer-readable storage medium of claim 17 further including program code, which when executed by the at least one data processor, further configured to perform operations comprising:
detecting an error in the delivery of the fluid to the user; and
stopping the delivery of the fluid to the user.

20. The non-transitory computer-readable storage medium of claim 19 further including program code, which when executed by the at least one data processor, further configured to perform operations comprising:
transmitting the error to a user device in wireless communication with the first slave infusion pump; and
displaying information associated with the error via the user device.

* * * * *